(12) United States Patent
Mori et al.

(10) Patent No.: US 7,662,852 B2
(45) Date of Patent: Feb. 16, 2010

(54) COMPOUNDS AND PREPARATIONS HAVING ANTIVIRAL EFFECT

(75) Inventors: Masao Mori, Toyama (JP); Haruo Saito, Toyama (JP); Hideo Nemoto, Toyama (JP); Naoiki Yamamoto, Ota-ku (JP); Masao Hattori, Toyama (JP)

(73) Assignee: Lead Chemical Co., Ltd., Toyama (JP)

(*) Notice: Subject to any disclaimer, the term of this patent is extended or adjusted under 35 U.S.C. 154(b) by 537 days.

(21) Appl. No.: 10/557,922

(22) PCT Filed: May 22, 2003

(86) PCT No.: PCT/JP03/06422

§ 371 (c)(1), (2), (4) Date: Dec. 22, 2005

(87) PCT Pub. No.: WO2004/103360

PCT Pub. Date: Dec. 2, 2004

(65) Prior Publication Data

US 2007/0066684 A1    Mar. 22, 2007

(51) Int. Cl.
- A01N 37/02 (2006.01)
- A61K 31/22 (2006.01)
- A23L 1/30 (2006.01)
- C07C 43/02 (2006.01)

(52) U.S. Cl. .................. 514/546; 554/229; 568/664

(58) Field of Classification Search .......... 514/546; 554/229; 568/664
See application file for complete search history.

(56) References Cited

U.S. PATENT DOCUMENTS 6,268,395 B1    7/2001    Hattori

FOREIGN PATENT DOCUMENTS

| JP | A-05-097888 | 4/1993 |
|---|---|---|
| JP | A-05-279329 | 10/1993 |
| JP | A-05-331067 | 12/1993 |
| JP | A-06-025158 | 2/1994 |
| JP | A-06-056825 | 3/1994 |
| JP | A-06-073004 | 3/1994 |
| JP | A-06-234641 | 8/1994 |
| JP | A-06-316524 | 11/1994 |
| JP | A-07-082292 | 3/1995 |
| JP | A-07-285877 | 10/1995 |
| JP | A-09-030974 | 2/1997 |
| JP | A-11-322789 | 11/1999 |
| WO | WO 01/82927 A1 | 11/2001 |

OTHER PUBLICATIONS

Raffanti S and Haas DW, Chapter 51 Antimicrobial Agents, "Goodman & Gilman's The Pharmacological Basis of Therapeutics, 10th ed." Hardman JG, Limbird LE, and Goodman AG, Eds., McGraw-Hill, New York, 2001.*

Carey FA and Sundberg RJ, Chapter 13, Section 13.1, "Advanced Organic Chemistry 3rd. Ed.", Plenum Press, New York, 1990, pp. 678-686 provided.*

Greene TW and Wuts PGM, "Protective Groups in Organic Synthesis," John Wiley & Sons, Inc., New York, 1991, Chapter 2, pp. 10-13, 88, and 89 provided.*

El-Mekkawy et al., "Inhibition of Cytopathic Effect of Human Immunodeficiency Virus Type-1 by Various Phorbol Derivatives," Chem. Pharm. Bull., 2002, vol. 50, No. 4, pp. 523-529.

El-Mekkawy et al., "12-O-Acetylphorbol-13-decanoate Potently Inhibits Cytopathic Effects of Human Immunodeficiency Virus Type 1 (HIV-1), without Activation of Protein Kinase C," Chem. Pharm. Bull., 1999, vol. 47, No. 9, pp. 1346-1347.

El-Mekkawy et al., "Anti-HIV-1 phorbol esters from the seeds of Croton tiglium," Phytochemistry, 2000, vol. 53, No. 4, pp. 457-464.

Maio et al., "Regulation of Expression Driven by Human Immunodeficiency Virus Type 1 and Human T-Cell Leukemia Virus Type 1 and Human T-Cell Leukemia Virus Type I Long Terminal Repeats in Pluripotential Human Embryonic Cells," J. Virol., 1988, vol. 62, No. 4, pp. 1398-1407.

Kinzel et al., "Stimulation of Choline Incorporation in Cell Cultures by Phorbol Derivatives and Its Correlation with Their Irritant and Tumor-Promoting Activity," Cancer Research, 1979, vol. 39, No. 7, pp. 2743-2750.

Chem. Abstr., vol. 70, No. 4, 1969, pp. 359-360, abstract No. 70: 47626, Kreibich et al. "Chemistry of Phorbol. V. Phorbol Ethers," Chemie, Biochemie. Biophysik. Biologie., 1968, vol. 23, No. 11, pp. 1444-1452.

* cited by examiner

Primary Examiner—San-ming Hui
Assistant Examiner—Paul Zarek
(74) Attorney, Agent, or Firm—Oliff & Berridge, PLC (57) ABSTRACT

An antiviral preparation comprising as an active ingredient, a phorbol derivative of formula 1:

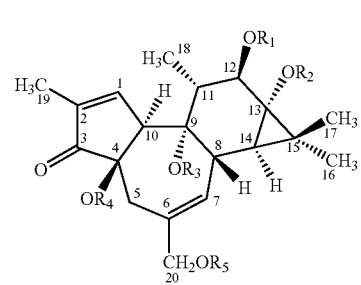

wherein is $R_1$ is —$(CH_2)_aX(CH_2)_bCH_3$, —$(CH_2)_cX(CH_2)_dYCH_3$, —$CO(CH_2)_eCH_3$ or —$(CH_2)_fCH_3$ $R_2$ is —$CO(CH_2)_nCH_3$, $R_3$, $R_4$ and $R_5$ are hydrogen atom, or an aliphatic or aromatic carboxylic acid residue, X and Y are O or S, and each of a-f and n is a number, and having a specific safety index $S.I.=CC_{50}/EC_{50}$ of 10 or more wherein $EC_{50}$ means a concentration at which HIV-1 induced cytopathogenic effect (CPE) in MT-4 cell is inhibited by 50%, and $CC_{50}$ means a concentration at which survival of MT-4 cell in a cell proliferation test is reduced by 50%. These preparations are particularly effective for human immuno-deficiency virus (HIV).

11 Claims, 4 Drawing Sheets

COMPOUNDS AND PREPARATIONS HAVING ANTIVIRAL EFFECT

TECHNICAL FIELD

The present invention relates to antiviral preparations containing a phorbol derivative having antiviral effect as an active ingredient, further a inhibitor against replication or maturity process of virus, and optionally other agents, such as an agent having an antiviral effect other than the phorbol derivative, an antidote for inhibiting or removing any side effect by the above-mentioned agents, particularly antiviral preparations effective for virus such as human immuno-deficiency virus (HIV).

BACKGROUND ART

Since human immuno-deficiency virus (HIV) causing acquired immuno-deficiency syndrome (AIDS) was found, investigations for developing effective anti-HIV drugs have been eagerly undertaken, and recently this field has been remarkably advanced. In the research and development of therapeutic agents for AIDS, other than the research and development of novel chemical agents having an anti-HIV effect, the search for natural substances having anti-HIV effect has been actively made, for example it is reported that compounds having several chemical structures from plants inhibit the replication of HIV-1 or enzymes involved therein (for example, see Che, 1991; Schinazi, 1992; Nasr, Cradock & Johnson, 1992; El-Mekkawy et al., 1995; El-Mekkawy, Meselhy, Kusumoto, Kadota, Hattori, Namba, 1998; Ng, Huang, Fong & Yeung, 1997; Kusumoto & Hattori, 1999).

Physiologically active substances from plants are relatively easily available from plants as raw material. In addition, there are many plants that are used as raw material for Japanese and Chinese medicine or folk remedies around the world, and there are also a great deal of accumulation of information on physiologically active substances. Therefore, the physiologically active substances from plants are expected as effective anti-HIV agents.

However, any physiologically active substances having anti-HIV effect from plants found to date do not have sufficient activity. In addition, as some of the above-mentioned substances from plants have harmful side effects such as toxicity, carcinogenicity and the like, it is difficult to select the most suitable substance as an antiviral agent such as anti-HIV agent or the like. Therefore, it is expected to find the substances having a high antiviral effect (for example, anti-HIV effect) and little harmful side effects, and to develop effective antiviral agents based on the finding for example anti-HIV agents.

The present inventors searched several Egyptian folk medicines with the guidance of anti-HIV effect in the process of search for natural AIDS therapeutic agents, and found that methanol-extraction or water-extraction of *Croton tiglium* seeds (crude drug name of the seeds: badou (巴豆, Crotonis Semen) inhibits HIV proliferation and cytopathogenic effect (CPE) in MT-4 cells in a lower concentration ($IC_{50}$ is 0.025 μg/mL or 2.0 μg/mL, respectively) than the cytotoxic concentration (selective index is 34.4 or 50.0, respectively) (Kawahata, Otake, Mori, Morimoto, Ueba, Kusumoto et al., 1996). The present inventors particularly found that a phorbol ester of tiglian type contained in *Croton tiglium*, in particular a specific phorbol derivative has an effect of strongly suppressing the proliferation of AIDS virus.

By the way, in the present anti-HIV therapy, the use of an antiviral agent alone is hardly carried out, and a highly active-retroviral therapy by using simultaneously a plurality of agents is mainly carried out. Behind the trend is the fact that a fully anti-HIV effect cannot be necessarily expected in case where a reverse transcriptase inhibitor, a protease inhibitor or the like usable for AIDS therapy is used alone as an anti-HIV agent.

That is, as the present anti-HIV agents merely suppress or inhibit the replication or maturity of AIDS virus, the AIDS therapy must continuously suppress or inhibit the replication or maturity of AIDS virus. On the other hand, AIDS virus cause mutation for each reverse transcription, and therefore it is apt to acquire any drug resistance, and thus it becomes clear that anti-HIV agents based on the mechanism of action in which the replication or maturity of AIDS virus is suppressed or inhibited is lowered in its clinical effects.

In order to compensate the above-mentioned disadvantages, for example 2-agent combination therapy with two reverse transcriptase inhibitors is performed to suppress the replication of virus. Further, even when the 2-agent combination therapy is applied, in case where AIDS virus resistance to the anti-HIV drug is induced owing to a long-term administration and the therapy does not lead to a sufficient therapeutic effect, a more effective 3-agent combination therapy, that is, for example a 3-agent combination therapy of two reverse transcriptase inhibitors of nucleoside type and one protease inhibitor is applied, and the long-term effect is observed by the clinical test.

As the anti-HIV drugs, currently reverse transcriptase inhibitors and protease inhibitors are commercially available, and integrase inhibitors and co-receptor agents, etc. are being developed.

Under the present state as mentioned above, several inhibitors or antiviral agents, or antidotes against the inhibitors or the antiviral agents are proposed as follows:

Regarding inhibitors: for example JP-A-5-279329 (1993) (HIV protease inhibitors having internal lactam ring), JP-A-5-331067 (1993) (inhibitors of retroviral protease), JP-A-6-25158 (1994) (substituted pyrrolidine derivatives and HIV protease inhibitors), JP-A-6-73004 (1994) (substituted pipecolinuc acid derivatives and HIV protease inhibitors), JP-A-7-285877 (1995) (reverse transcriptase inhibitors of HIV-1), and JP-A-11-322789 (1999) (amino acid derivatives);

Regarding antiviral agents: for example JP-A-5-97888 (1993) (novel oxetanocine derivatives, salts thereof and antiviral agents), JP-A-6-56825 (1994) (benzodiazepines), JP-A-6-234641 (1994) (antiviral combinations), JP-A-6-316524 (1994) (anti-AIDS virus agents), and JP-A-7-82292 (1995) (novel glycyrrhetinic acid related compounds or salts thereof); and regarding antidotes: for example JP-A-9-30974 (1997) (elimination of toxicity and adverse effect of AIDS virus inhibitor or the like and the production process thereof).

As to the mechanism of action of anti-HIV drugs, it is supposed that there are some active points in the process from the replication to maturity in the infected cells caused by the bonding of HIV on normal host cells (human CD4 positive T lymphocytes or macrophages). Hereinafter, the replication and maturity processes of HIV virus are briefly described based on FIGS. 1 and 2.

Figure 1:
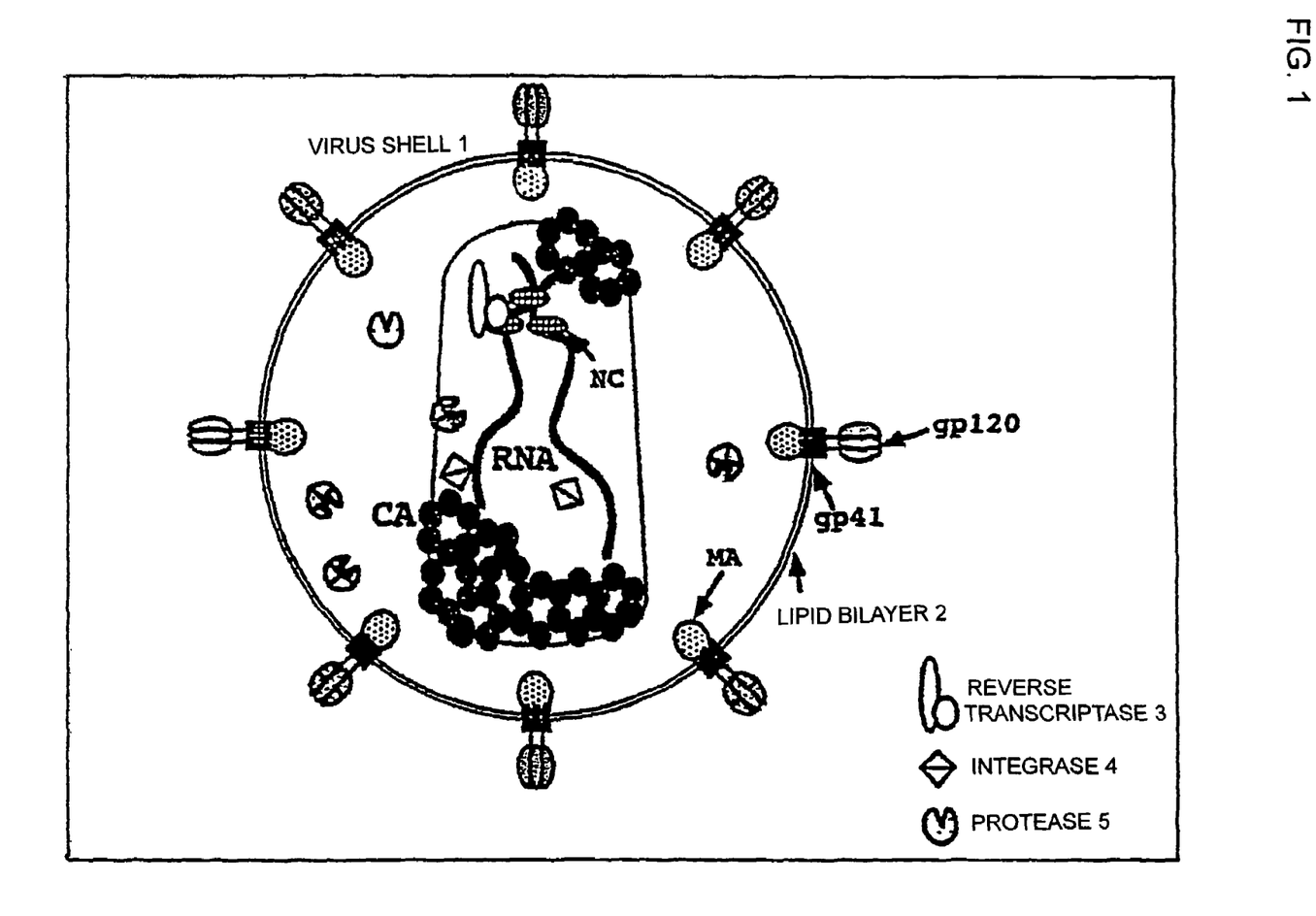
FIG. 1 is a figure showing the general structure of HIV virus.

FIG. 1 shows a general structure of HIV virus. Virus shell 1 is composed of lipid bilayer 2, and has a structure composed of matrix/protein (MA) with gp41 and gp120 on the surface thereof. In the virus shell 1, core/protein (CA), nucleocapsid/protein (NC), RNA, reverse transcriptase 3, integrase 4 and protease 5, etc. are present.

Figure 2:
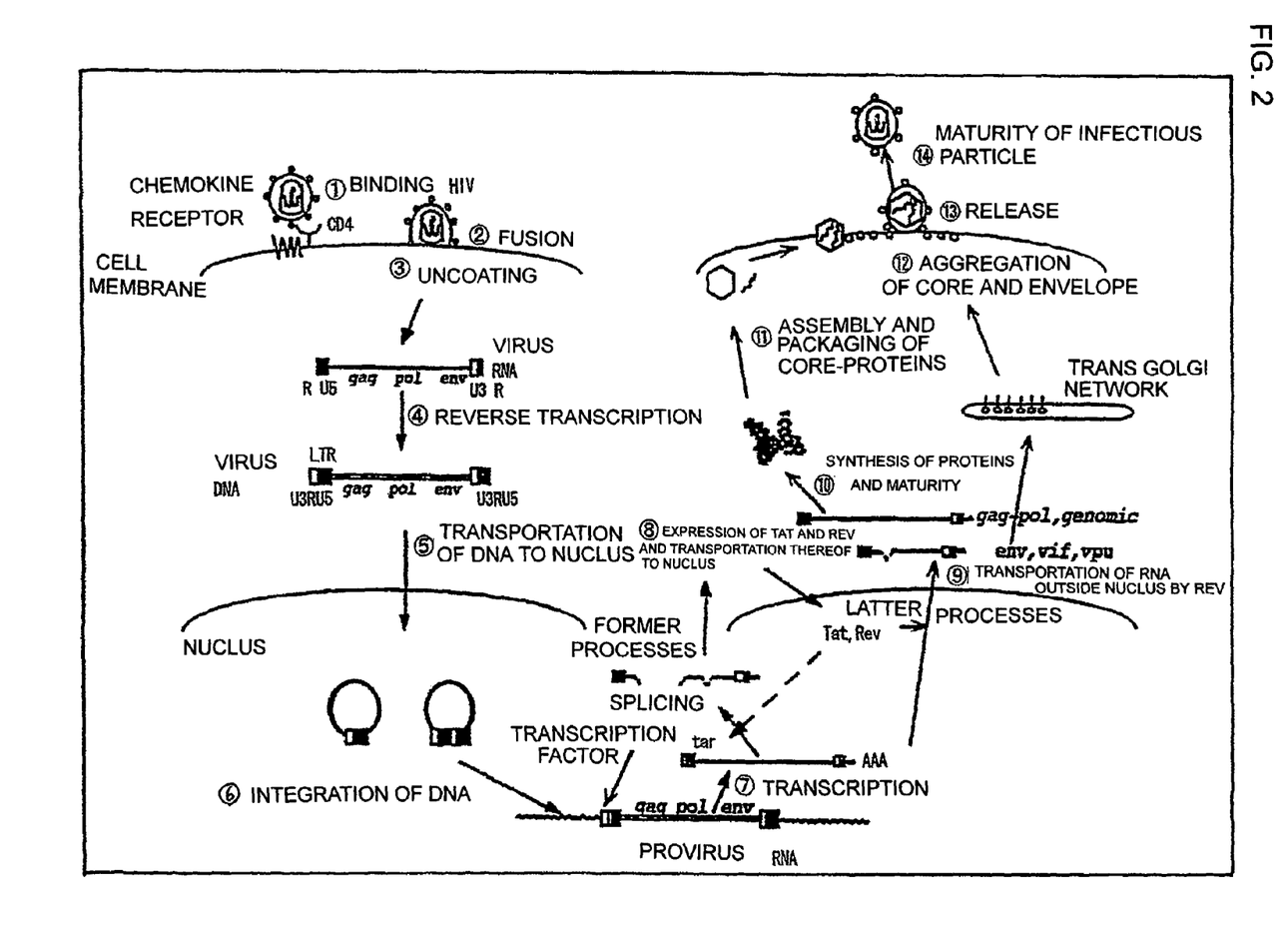
FIG. 2 is a figure showing the mechanism of the replication process or maturity process of HIV virus.

HIV virus having the structure shown in FIG. 1 is replicated and matured according to the mechanism shown in FIG. 2. In FIG. 2, a virus particle having envelope (virus shell 1) binds to a specific cell membrane molecule (receptor; chemokine and CD4) (process ①). Then, the virus particle is fused to the cell membrane by use of the envelope (process ②), and invades the cell. Uncoated (process ③) virus replicates DNA by reverse-transcribing RNA by its own reverse transcriptase (process ④), the replicated DNA is transported in the cell nucleus (process ⑤). The DNA in the cell nucleus is integrated with integrase (process ⑥) to form provirus. Further, the genetic information of HIV is amplified and transcribed, the proteins of HIV are synthesized by the action of protease contained in HIV virus (process ⑦), the assembly of core proteins (process ⑧) and the aggregation of envelopes (process ⑨) are performed to complete the maturity of infectious virus particle (process ③). In addition, unknown active parts or mechanism of action that inhibits virus in the process from binding to maturity is assumed (process ⑪). Also, the formation, release and maturity of HIV virus by trans Golgi network are performed (processes ⑫, ⑬ and ⑨).

The present AIDS therapy is centered on the use of anti-HIV drug composed of two agents: an agent for inhibiting the reverse transcriptase (inhibiting process ④) by which RNA is transcribed to DNA in the process from the binding of HIV virus on cell membrane to the integration in the mechanism shown in FIG. 2, and an agent for inhibiting protease involved in the synthesis of core proteins (inhibiting process ⑦) in the late process to the maturity of the provirus. And, highly active anti-retroviral therapy in which two or more of these agents are combined is attempted.

On the other hand, the above-mentioned specific phorbol derivatives do not have the above-mentioned representative two anti-HIV effects of the inhibition of reverse transcriptase and the inhibition of protease, and it is expected that the derivatives have another anti-HIV effect, that is, an anti-HIV effect for inhibiting the process from the binding of HIV virus on host cell to the fusion thereto (inhibiting processes ① and ②).

Therefore, it is expected that the use of a combination of a specific phorbol derivative with one or more of the above-mentioned several inhibitors (or the conventional anti-HIV drugs), that is, the use of so-called cocktail products having such a constitution exerts a further effective anti-HIV effect compared with the conventional anti-HIV drugs as the cocktail products act simultaneously on plural processes involved in the replication or maturity of HIV virus.

The present invention is made based on the above-mentioned standpoints, and an object thereof is to provide an antiviral agent (for example anti-HIV agent) having a further high anti-viral effect compared with the prior known antiviral agents, and having little harmful side effects.

DISCLOSURE OF INVENTION

A first invention of the present application relates to an antiviral preparation characterized by comprising as an active ingredient, at least a phorbol derivative of formula 1:

wherein $R_1$ is a group of —$(CH_2)_aX(CH_2)_bCH_3$ wherein X is O or S, a is a number of 1 to 3, and b is a number of 0 to 5, a group of —$(CH_2)_cX(CH_2)_dYCH_3$ wherein X and Y are O or S, c is a number of 1 to 3, and d is a number of 1 to 5, a group of —$CO(CH_2)_eCH_3$ wherein e is a number of 0 to 12, or a group of —$(CH_2)_fCH_3$ wherein f is a number of 0 to 5, $R_2$ is a group of —$CO(CH_2)_nCH_3$ wherein n is a number of 3 to 12, and $R_3$, $R_4$ and $R_5$ are independently of one another, hydrogen atom, or an aliphatic or aromatic carboxylic acid residue, and having a specific safety index $S.I.=CC_{50}/EC_{50}$ of 10 or more wherein $EC_{50}$ means a concentration at which HIV-1 induced cytopathogenic effect (CPE) in MTA-4 cell is inhibited by 50%, and $CC_{50}$ means a concentration at which survival of MT-4 cell in a cell proliferation test is reduced by 50%.

A second invention of the present application relates to the antiviral preparation as set forth in the first invention, wherein $R_1$ in formula 1 is a group of —$(CH_2)_aX(CH_2)_bCH_3$ wherein X is O or S, a is a number of 1 to 3, and b is a number of 0 to 5.

A third invention of the present application relates to the antiviral preparation as set forth in the first invention, wherein $R_1$ in formula 1 is a group of —$(CH_2)_cX(CH_2)_dYCH_3$ wherein X and Y are O or S, c is a number of 1 to 3, and d is a number of 1 to 5.

A fourth invention of the present application relates to the antiviral preparation as set forth in the first invention, wherein $R_1$ in formula 1 is a group of —$CO(CH_2)_eCH_3$ wherein e is a number of 0 to 12.

A fifth invention of the present application relates to the antiviral preparation as set forth in the first invention, wherein $R_1$ in formula 1 is a group of —$(CH_2)_fCH_3$ wherein f is a number of 0 to 5.

A sixth invention of the present application relates to a process for producing the phorbol derivative of formula 1 as set forth in the first invention, comprising: converting a group of —$CH_2OH$ on a naturally occurring or synthetic intermediate phorbol of formula 2:

into a group of —$CH_2OL$ wherein L is a protective group, to produce a compound of formula reacting the compound with a compound of $CH_3(CH_2)_nCOCl$ wherein n is the same meaning as the definition in the first invention of the present application, to produce a compound of formula reacting the compound with a compound of $R_1Cl$ wherein $R_1$ is the same meaning as the definition in the first invention of the present application, to produce a compound of formula further converting a group of —$CH_2OL$ on the resulting compound into a group of —$CH_2OH$.

A seventh invention of the present application relates to an anti-HIV virus preparation comprising at least one of phorbol derivatives of formula 1 as set forth in the first invention, and at least one of other agents having anti-HIV effect.

An eighth invention of the present application relates to the anti-HIV virus preparation as set forth in the seventh invention, characterized in that the other agent having anti-HIV effect is a reverse transcriptase inhibitor.

A ninth invention of the present application relates to the anti-HIV virus preparation as set forth in the seventh invention, characterized in that the other agent having anti-HIV effect is an agent that inhibits an integration of DNA mediated by an integrase.

A tenth invention of the present application relates to the anti-HIV virus preparation as set forth in the seventh invention, characterized in that the other agent having anti-HIV effect is an agent that suppresses a transcription of provirus.

An eleventh invention of the present application relates to the anti-HIV virus preparation as set forth in the seventh invention, characterized in that the other agent having anti-HIV effect is an agent that inhibits a synthesis of core protein mediated by a protease.

A twelfth invention of the present application relates to the anti-HIV virus preparation as set forth in the seventh invention, characterized in that the other agent having anti-HIV effect is an agent that suppresses an assembly and packaging of core proteins.

A thirteenth invention of the present application relates to the anti-HIV virus preparation as set forth in the seventh invention, characterized in that the other agent having anti-HIV effect is an agent that suppresses an aggregation of core proteins and extra-shell proteins.

A fourteenth invention of the present application relates to the anti-HIV virus preparation as set forth in the seventh invention, characterized in that the other agent having anti-HIV effect is an agent that suppresses a maturity of infectious virus particles released and escaped from cell membrane.

BEST MODE FOR CARRYING OUT THE INVENTION

In the phorbol derivatives of formula 1, $R_1$, $R_2$, $R_3$, $R_4$ and $R_5$ mean the groups in the defined scope. The aliphatic carboxylic acid residues or the aromatic carboxylic acid residues mean RCO moiety left after the removal of OH moiety from an aliphatic or aromatic carboxylic acid of general formula: RCOOH wherein R is an aliphatic group or an aromatic group, and specifically may be for example acetyl group, benzyl group, tigloyl group and the like.

The phorbol derivative of formula 1, as a preferable embodiment, can be produced by:

converting a group of —$CH_2OH$ on a naturally occurring or synthetic intermediate phorbol of formula 2:

into a group of —$CH_2OTBS$, to produce a compound of formula reacting the compound with a compound of $CH_3(CH_2)_nCOCl$ wherein n is a number of 3 to 12, to produce a compound of formula reacting the compound with a compound of $R_1Cl$ wherein $R_1$ is the same meaning as the definition in claim 1, to produce a compound of formula further converting a group of —$CH_2OTBS$ on the resulting compound into a group of —$CH_2OH$.

A lot of the phorbol derivatives of formula 1 have excellent antiviral effect, and therefore they can be used as an active ingredient for the antiviral preparations of the present invention, for example anti-HIV agents. However, as the phorbol derivatives of formula 1 involve those having a low antiviral effect, or those having harmful side effects, it is required to select those having a specific safety index $S.I.=CC_{50}/EC_{50}$ of 10 or more wherein $EC_{50}$ means a concentration at which HIV-1 induced cytopathogenic effect (CPE) in MT-4 cell is inhibited by 50%, and $CC_{50}$ means a concentration at which survival of MT-4 cell in a cell proliferation test is reduced by 50%. The antiviral preparations containing the phorbol derivative of formula 1 as an active ingredient can effectively inhibit the processes ① and ② in the mechanism of the life cycle of HIV shown in FIG. 2.

In addition, the other agents having anti-HIV-effect in the antiviral preparation of the present invention are preferably at least one selected from the following group:
(1) a reverse transcriptase inhibitor;
(2) an agent that inhibits an integration of DNA mediated by an integrase;
(3) an agent that suppresses a transcription of provirus;
(4) an agent that inhibits a synthesis of core protein mediated by a protease;
(5) an agent that suppresses an assembly and packaging of core proteins;
(6) an agent that suppresses an aggregation of core proteins and extra-shell proteins; and
(7) an agent that suppresses a maturity of infectious virus particles released and escaped from cell membrane.

These agents (1) to (7) are used in a combination with the phorbol derivative of formula 1, and can be suitably selected depending on intended purpose. When the antiviral preparation of the present invention is used as an anti-HIV drug, the phorbol derivative of formula 1 can be used for example in a combination with (1) a reverse transcriptase inhibitor and/or (4) an agent that inhibits a synthesis of core protein mediated by a protease.

Specifically, (1) reverse transcriptase inhibitors are for example zidovudine (AZT), didanosine (ddI), zalcitabine (ddC), lamivudine (3TC), sanilvudine (d4T), abacavir (ABC), zidovudine/lamivudine (AZT/3TC), nevirapine (NVP), efavirenez (EFV), N'-[1(S)-benzyl-3-[4a(S),8a(S),3(S)-tert-butylcarbamoyl]decahydro-isoquinolin-2-yl]-2(R)-hydroxypropyl-]-N"-(quinolin-2-yl carbamoyl)-L-asparagineamide (Ro31-8959) or (+)-S-4,5,6,7-tetrahydro-5-methyl-6-(3-methyl-2-butenyl)imidazo[4,5,1-jk][1,4]benzodiazepine-2(1H)-thion (R-82913, TIBO), or pharmaceutically acceptable derivatives thereof.

In addition, (4) agents that inhibits a synthesis of core protein mediated by a protease are for example indinavir (IDV), saquinavir (SQV), vitonavir (RTV), nelfinavir (NFV) or amprenavir (APV), or pharmaceutically acceptable derivatives thereof.

The antiviral preparations of the present invention can be varied into several forms depending on actual type of its usage. In case where effects for plural viruses requested for example, specifically for example in case where sterilization of subjects polluted with not only HIV virus but also other virus, or therapy of patients infected with not only HIV virus but also other virus is performed, further other antiviral agents such as dideoxyadenosine (DDA), foscanet, or the like can be simultaneously used.

When other agents having anti-HIV effect are simultaneously used, side effects of the agents become problematic in some cases. Thus, in such case, suitable antidotes, the antidotes against the phorbol derivatives of formula 1 or other antiviral agents other than them can be further blended and used.

The antiviral preparations of the present invention can be used for several purposes if the purpose is suitable. The purposes include for example the therapy of human or animals other than human suffering from viral diseases, sterilization of subjects polluted with virus, preventive application (coating, spraying, scattering, etc.) to subjects that may be polluted with virus, and the like. In addition, the type of usage of the antiviral preparations according to the present invention can be suitably selected depending on the purpose. For example, the type of usage of the antiviral preparations according to the present invention can be powder, granule, tablet, solution, emulsion, dispersion, paste or the like.

EXAMPLES a) Instrumental Analysis

Optical rotations were measured with DIP-360 automatic optical rotation detector (JASCO, Kyoto, Japan). Infrared absorption spectra were recorded with FT/IR-230 spectrometer (JASCO, Kyoto, Japan). Ultraviolet absorption spectra were measured with UV-2200UV-VIS spectrophotometer (Shimadzu, Kyoto, Japan). NMR spectra were measured with Varian Unity plus 500 ($^1$H, 500 MHz; $^{13}$C, 125 MHz) photometer, and chemical shifts (δ) were indicated with tetramethyl silane (TMS) as a standard.

b) Chromatography

Column Chromatography
Silica gel 60 (70-230 mesh, Merk), ODS Cosmobil 140 C18-OPN (Nacalai Tesque, Kyoto, Japan).

c) Reagents and Enzymes

Any reagents and enzymes used were those commonly used in the art.

Example 1

Synthesis of Phorbol Derivative

Figure 3:
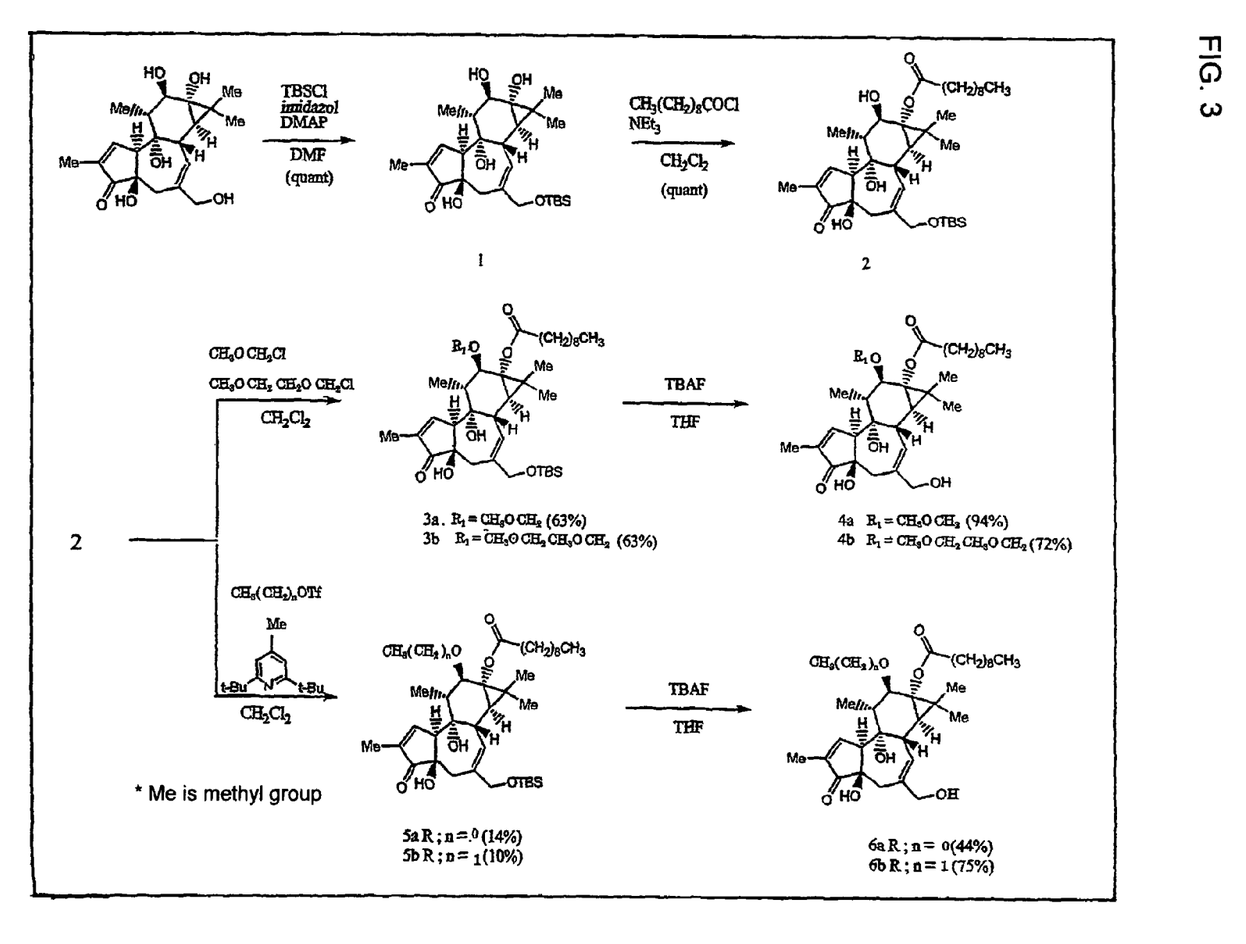
FIG. 3 is a figure showing the formation mechanism of several phorbol derivatives.

1) TBS Treatment
Under Ar flow, anhydrous DMF (2 ml) solution of phorbol (364 mg, 1 mmol), imidazole (201 mg, 3 mmol) and N,N-dimethylaminopyridine (12 mg, 0.1 mmol) was cooled with ice, anhydrous DMF (2 ml) solution of t-butyldimethylsilyl chloride (166 mg, 1.1 mmol) was added, and stirred under cooling with ice for 1 hour. The reaction solution was subjected to directly silica gel chromatography (AcOEt), and the solvent of the fraction containing products was distilled off under a reduced pressure. The obtained residue was suspended in $CH_2Cl_2$-hexane (1:1) and after cooling, crystals separated out were filtered out with suction and dried to obtain 271 mg of colorless crystals. The filtrate was dried under a reduced pressure, and the resulting residue was subjected to silica gel chromatography (AcOEt) again to obtain 21 mg of colorless crystals (compound 1 in FIG. 3). In total, 292 mg (61%). Mp (melting point): 270-273° C. (decomposition).

$^1$H-NMR (acetone-$d_6$): 0.05 (3H, s), 0.06 (3H, s), 0.71 (1H, d, J=5.6 Hz), 0.88 (9H, s), 1.07 (3H, d, J=6.4 Hz), 1.16 (3H, s), 1.23 (3H, s), 1.69 (3H, dd, J=3.0, 1.3 Hz), 1.95-2.00 (1H, m), 2.46 (2H, s), 3.09-3.14 (2H, m), 3.24 (1H, bs), 3.51 (1H, br), 4.05 (2H, s), 4.09 (1H, br), 4.10 (1H, d, J=9.8 Hz), 4.65 (1H, s), 5.61 (1H, d, J=5.6 Hz), 7.58 (1H, s); $^{13}$C-NMR (acetone-$d_6$): −5.14, 10.22, 15.53, 17.81, 18.78, 24.08, 26.22, 26.46, 37.15, 38.25, 40.12, 46.06, 58.23, 62.99, 68.64, 74.50, 78.79, 81.43, 130.31, 133.14, 140.90, 159.75, 208.49; IR (KBr) $cm^{-1}$: 3315, 1675; Anal. Calcd for $C_{26}H_{42}O_6Si$ Calculated: C, 65.24; H, 8.84. Measured: C, 64.95; H, 8.69; $[\alpha]_D^{25}$=+83.39 (c=0.85, MeOH).

2) Decanoylation
Under Ar flow, anhydrous $CH_2Cl_2$ (1 ml) solution of TBS form (compound 1 in FIG. 3; 48 mg, 0.1 mmol) and triethylamine (42 μl, 0.3 mmol) was cooled with ice, decanoyl chloride (41μ, 0.2 mmol) was added and stirred at room temperature for 3 hours. The reaction solution was diluted with $CH_2Cl_2$, and washed with 10% HCl, saturated $NaHCO_3$ water and saturated sodium chloride water in order, and after drying over $MgSO_4$, the solvent was distilled out under a reduced pressure. The residue was subjected to silica gel chromatography ($CH_2Cl_2$—AcOEt=4:1) to obtain colorless oil (compound 2 in FIG. 3; 47 mg, 74%).

$^1$H-NMR ($CDCl_3$): 0.04 (3H, s), 0.05 (3H, s), 0.86-0.89 (12H, m), 0.99 (1H, d, J=5.6 Hz), 1.04 (3H, d, J=6.8 Hz), 1.19 (3H, s), 1.22-1.36 (17H, m), 1.58-1.65 (2H, m), 1.76 (3H, dd, J=3.0, 1.3 Hz), 1.97-2.04 (1H, m), 2.33-2.37 (3H, m), 2.46 (1H, d, J=18.8 Hz), 2.71 (1H, s), 3.13 (2H, br), 3.96 (1H, d, J=9.8 Hz), 4.00 (2H, s), 5.59 (1H, d, J=5.8 Hz), 7.56 (1H, d, J=1.3 Hz); $^{13}$C-NMR ($CDCl_3$): −5.29, 10.11, 14.10, 15.07, 16.91, 18.36, 22.63, 23.65, 24.76, 25.81, 25.91, 26.59, 29.09, 29.20, 29.22, 29.36, 31.81, 34.26, 35.46, 38.32, 38.99, 44.90, 56.80, 67.90, 73.49, 77.53, 78.21, 127.63, 132.90, 140.54, 160.45, 176.86, 208.96; IR (neat) 3396, 1706 $cm^{-1}$; MS m/z 575 ($M^+$-t-Bu); HRMS Calcd for $C_{32}H_{51}O_7Si$ Calculated: 575.3404. ($M^+$-t-Bu), Measured: 575.3432; $[\alpha]_D^{25}$=+65.95 (c=0.71, $CHCl_3$).

3) MOM Treatment
Under Ar flow, to anhydrous $CH_2Cl_2$ (0.5 ml) solution of decanoylated form (compound 2 in FIG. 3; 16.1 mg, 0.025 mmol) and diisopropylethylamine (14 ml, 0.075 mmol), chloromethyl methyl ether (3.8 ml, 0.05 mmol) was added and stirred at room temperature for 20 hours. The reaction solution was diluted with $CH_2Cl_2$, and washed with 10% HCl, saturated $NaHCO_3$ water and saturated sodium chloride water in order, and after drying over $MgSO_4$, the solvent was distilled out under a reduced pressure. The residue was subjected to silica gel chromatography ($CH_2Cl_2$—AcOEt=9:1) to obtain colorless oil (compound 3a in FIG. 3; 10.7 mg, 63%).

$^1$H-NMR ($CDCl_3$): 0.04 (3H, s), 0.05 (3H, s), 0.87 (9H, s), 0.88 (3H, t, J=7.2 Hz), 0.97 (1H, d, J=5.6 Hz), 1.05 (3H, d, J=6.4 Hz), 1.18 (3H, s), 1.22-1.33 (17H, m), 1.77 (3H, dd, J=3.0, 1.3 Hz), 2.02-2.07 (1H, m), 2.18 (1H, s), 2.29-2.36 (2H, m), 2.38 (1H, d, J=18.8 Hz), 2.47 (1H, d, J=18.8 Hz), 3.12 (1H, t, J=5.6 Hz), 3.23 (1H, bs), 3.36 (3H, s), 3.94 (1H, d, J=9.4 Hz), 4.00 (2H, s), 4.54 (1H, d, J=6.4 Hz), 4.88 (1H, d, J=6.8 Hz), 5.61 (1H, d, J=6.3 Hz), 5.65 (1H, s), 7.61 (1H, s); $^{13}$C-NMR ($CDCl_3$): −5.30, −5.28, 10.11, 14.10, 15.16, 16.80, 18.36, 22.64, 23.84, 24.56, 25.55, 25.92, 29.07, 29.23, 29.24, 29.38, 31.83, 34.53, 36.08, 38.39, 39.11, 44.23, 55.68, 56.12, 65.56, 68.20, 73.73, 77.76, 79.80, 95.05, 128.46, 132.44, 139.85, 161.20, 176.19, 209.19; IR (neat) $cm^{-1}$: 3404, 1709; MS m/z 676 ($M^+$); HRMS Calcd for $C_{38}H_{64}O_8S$ Calculated: 676.43704. ($M^+$), Measured: 676.4402; $[\alpha]_D^{25}$=+78.75 (c=0.53, $CHCl_3$).

4) Desilylation
Under Ar flow, anhydrous THF (0.5 ml) solution of MOM form (compound 3a in FIG. 3; 45 mg, 0.067 mmol) was cooled with ice, tetra-n-butylammonium fluoride (1 M THF solution, 0.2 ml, 0.2 mmol) was added, and stirred under cooling with ice for 1.5 hour. Saturated $NaHCO_3$ water was added to the reaction solution, and the resulting solution was extracted with $CHCl_3$, and after drying over $MgSO_4$, the solvent was distilled out under a reduced pressure. The residue was subjected to silica gel chromatography ($CH_2Cl_2$—AcOEt=4:1) to obtain colorless oil (compound 4a (sample NPB-11) in FIG. 3; 35 mg, 94%).

$^1$H-NMR ($CDCl_3$): 0.88 (3H, t, J=7.3 Hz), 1.00 (1H, d, J=5.6 Hz), 1.06 (3H, d, J=6.8 Hz), 1.19 (3H, s), 1.22-1.35 (18H, m), 1.78 (3H, d, J=1.7 Hz), 2.02-2.07 (1H, m), 2.24 (1H, s), 2.29-2.35 (2H, m), 2.46 (1H, d, J=18.8 Hz), 2.53 (1H, d, J=18.8 Hz), 3.18 (1H, t, J=5.6 Hz), 3.23 (1H, s), 3.36 (3H, s), 3.94 (1H, d, J=9.8 Hz), 3.98 (1H, d, J=12.8 Hz), 4.04 (1H, d, J=12.8 Hz), 4.54 (1H, d, J=6.8 Hz), 4.88 (1H, d, J=6.8 Hz), 5.67 (1H, d, J=4.7 Hz), 5.76 (1H, s), 7.61 (1H, s); $^{13}$C-NMR ($CDCl_3$): 10.13, 14.11, 15.21, 16.78, 22.65, 23.84, 24.58, 25.61, 29.08, 29.23, 29.25, 29.38, 31.84, 34.52, 36.05, 38.60, 39.06, 44.20, 55.71, 56.17, 65.52, 68.04, 73.62, 77.97, 79.67, 95.06, 129.37, 132.68, 140.27, 161.09, 176.32, 209.08; IR (neat) $cm^{-1}$: 3409, 1709; MS m/z 501 ($M^+$-$OCH_2OCH_3$); HRMS Calcd for $C_{30}H_{45}O_6$ Calculated: 501.3216. ($M^+$-$OCH_2OCH_3$), Measured: 501.3200; $[\alpha]_D^{25}$=+89.27 (c=0.11, $CHCl_3$).

5) MEM Treatment

Under Ar flow, to anhydrous $CH_2Cl_2$ (3 ml) solution of decanoyl form (compound 2 in FIG. 3; 234 mg, 0.37 mmol) and diisopropylethylamine (0.051 ml, 0.44 mmol), chloromethyl methyl ether (0.13 ml, 0.74 mmol) was added and stirred at room temperature for 20 hours. The reaction solution was diluted with $CH_2Cl_2$, and washed with 10% HCl, saturated $NaHCO_3$ water and saturated sodium chloride water in order, and after drying over $MgSO_4$, the solvent was distilled out under a reduced pressure. The residue was subjected to silica gel chromatography ($CH_2Cl_2$—AcOEt=5:1) to obtain colorless oil (compound 3b in FIG. 3; 10.7 mg, 63%).

$^1$H-NMR ($CDCl_3$) 0.02 (6H, s), 0.85 (9H, s), 0.88 (1H, d, J=5.8 Hz), 0.98 (3H, d, J=6.3 Hz), 1.13 (3H, s), 1.20-1.24 (17H, m), 1.57-1.68 (2H, m), 1.72 (3H, m), 2.31-2.28 (3H, m), 2.46 (1H, d, J=7.9 Hz), 2.72 (1H, Br), 3.08 (1H, m), 3.17 (1H, Br), 3.30 (1H, d, J=4.4 Hz), 3.35 (3H, s), 3.50-3.53 (2H, m), 3.61-3.73 (2H, m), 3.894 (1H, d, J=9.6 Hz), 3.97 (2H, s), 4.64 (1H, d, J=6.6 Hz), 4.94 (1H, d, J=6.6 Hz), 5.57 (1H, br), 5.60 (1H, s), 7.55 (1H, s); $^{13}$C-NMR ($CDCl_3$): −4.98 (q), 10.33 (q), 14.33 (q), 15.38 (s), 17.11 (q), 18.58 (q), 22.87 (t), 24.03 (q), 24.79 (t), 25.77 (s), 26.15 (q), 29.34 (t), 29.45 (t), 29.62 (t), 32.04 (t), 34.73 (t), 36.35 (d), 38.52 (t), 39.31 (d), 44.31 (d), 56.31 (d), 59.14 (q), 65.62 (t), 67.23 (t), 68.30 (t), 71.85 (s), 73.82 (s), 77.88 (d), 80.15 (d), 93.82 (t), 128.42 (d), 132.45 (s), 139.99 (s), 160.95 (d), 176.12 (s), 208.97 (s); IR (neat) $cm^{-1}$: 3411, 1711; MS m/z 720 ($M^+$); HRMS Calcd for $C_{40}H_{68}O_9Si$ Calculated: 720.4633. ($M^+$), Measured: 720.4622; $[\alpha]_D^{25}$=+79.98 (c=0.90, $CHCl_3$).

6) Elimination of TBS

Under Ar flow, anhydrous THF (1.5 ml) solution of MEM form (compound 3b in FIG. 3; 147 mg, 0.204 mmol) was cooled with ice, tetra-n-butylammonium fluoride (1 M THF solution, 0.6 ml, 0.612 mmol) was added, and stirred under cooling with ice for 1.5 hour. Saturated $NH_4Cl_3$ water was added to the reaction solution, and the resulting solution was extracted with $CHCl_3$, and after drying over $MgSO_4$, the solvent was distilled out under a reduced pressure. The residue was subjected to silica gel chromatography ($CH_2Cl_2$—AcOEt=4:1) to obtain colorless oil (compound 4b (sample NPB-12) in FIG. 3; 89 mg, 72%).

$^1$H-NMR ($CDCl_3$): 0.86 (3H, t, J=7.1 Hz), 0.99 (3H, t, J=6.2 Hz), 1.16 (3H, s), 1.21-1.25 (18H, m), 1.58 (2H, m), 1.72 (3H, d, J=1.4 Hz), 2.46-2.50 (2H, m), 2.29-2.32 (2H, m), 3.17-3.18 (2H, m), 3.33 (1H, d, J=4.4 Hz), 3.36 (3H, s), 3.52 (2H, t, J=4.9 Hz), 3.64-3.75 (2H, m), 3.95 (2H, t, J=10.3 Hz), 4.65 (1H, d, J=6.9 Hz), 4.94 (1H, d, J=6.9 Hz), 5.63 (1H, d, J=5.2 Hz), 5.75 (1H, s), 7.55 (1H, s); $^{13}$C-NMR ($CDCl_3$): 10.36 (q), 14.36 (q), 15.48 (s), 17.09 (q), 22.90 (t), 24.05 (q), 24.84 (t), 25.85 (s), 29.37 (t), 29.47 (t), 29.63 (t), 32.06 (t), 34.76 (t), 36.31 (d), 38.68 (t), 39.21 (d), 44.31 (d), 56.26 (d), 59.18 (q), 65.66 (s), 67.28 (t), 68.16 (t), 71.86 (t), 73.75 (s), 78.24 (s), 80.13 (d), 93.96 (t), 129.33 (d), 132.71 (s), 140.54 (s), 160.99 (d), 176.28 (s), 209.14 (s); IR (neat) $cm^{-1}$: 3406, 1709; MS m/z 588 ($M^+$-$H_2O$); HRMS Calcd for $C_{34}H_{54}O_9$ Calculated: 606.3768. ($M^+$), Measured: 606.3779; $[\alpha]_D^{25}$=+85.88 (c=1.00, $CHCl_3$).

7) Methylation

Under Ar flow, to anhydrous dichloromethane solution of alcohol form (compound 2 in FIG. 3; 165 mg, 0.26 mmol), 2,6-di-t-butyllutidine (474 mg, 1.82 mmol) and MeOTf (0.122 ml, 1.09 mmol) were added, and stirred at room temperature for 20 hours. Then, the solution was made basic with pyridine, and the organic phase washed with saturated sodium hydrogen carbonate water and saturated sodium chloride was dried over magnesium sulfate and filtered, and then the solvent was distilled off. The residue was separated through silica gel chromatography ($CH_2Cl_2$—AcOEt=5:1) to obtain methylated form (compound 5a in FIG. 3; 23 mg, 14%) as colorless oily substance.

$^1$H-NMR ($CDCl_3$): 0.05 (3H, s), 0.07 (3H, s), 0.89 (9H, s), 0.97 (3H, s), 1.02 (2H, d, J=6.6 Hz), 1.14 (3H, s), 1.23-1.26 (18H, m), 1.61-1.68 (6H, m), 1.79 (3H, s), 2.01-2.17 (4H, m), 2.21-2.26 (1H, m), 2.33-2.39 (4H, m), 2.43-2.49 (1H, m), 2.62 (1H, br), 3.19 (1H, br), 3.24 (3H, s), 3.43 (1H, d, J=8.0 Hz), 3.97 (1H, d, J=1.3 Hz), 4.00 (2H, s), 4.31 (1H, s), 5.65 (1H, s), 7.46 (1H, s); $^{13}$C-NMR ($CDCl_3$): −4.91 (q), 1.35 (s), 10.46 (q), 14.41 (q), 16.11 (q), 17.43 (q), 22.95 (t), 23.61 (q), 25.22 (t), 25.98 (s), 26.19 (q), 27.53 (s), 29.39 (t), 29.54 (t), 29.68 (t), 29.97 (t), 32.12 (t), 34.32 (t), 35.09 (d), 38.22 (d), 38.98 (t), 46.48 (d), 48.89 (d), 52.20 (q), 68.14 (t), 69.69 (s), 73.71 (s), 78.48 (d), 83.90 (q), 128.70 (d), 133.72 (s), 137.68 (s), 160.31 (d), 208.97 (s); IR (neat) $cm^{-1}$: 3484, 1711; $[\alpha]_D^{25}$=+62.30 (c=0.99, $CHCl_3$).

8) Desilylatin

Under Ar flow, anhydrous THF solution of silylated form (compound 5a in FIG. 3; 23 mg, 0.0356 mmol) was cooled with ice, tetra-n-butylammonium fluoride (1 M THF solution, 0.071 ml, 0.0711 mmol) was added, and stirred at room temperature for 90 minutes. The reaction was stopped with saturated ammonium chloride aqueous solution, and the organic phase obtained by extracting with chloroform was dried over magnesium sulfate, filtrated and the solvent was distilled out. The residue was separated through silica gel chromatography (AcOEt) to obtain alcohol form (compound 6a (sample NPB-13) in FIG. 3; 8 mg, 0.0156 mmol, 44%) as colorless oily substance.

$^1$H-NMR ($CDCl_3$): 0.86-0.91 (3H, m), 0.97-1.04 (4H, m), 1.15 (3H, s), 1.24-1.27 (16H, m), 1.61-1.68 (4H, m), 1.78 (2H, q, J=1.4 Hz), 2.04-2.17 (1H, m), 2.34-2.38 (2H, m), 2.42-2.51 (2H, m), 3.20 (1H, s), 3.25 (3H, s), 3.40 (1H, m), 3.98 (1H, d, J=9.1 Hz), 4.07 (2H, s), 4.31 (1H, s), 5.67 (1H, s), 7.47 (1H, s); $^{13}$C-NMR ($CDCl_3$): 1.02, 10.15, 14.10, 15.78, 17.20, 22.62, 24.89, 24.98, 27.22, 29.06, 29.21, 29.35, 29.64, 34.00, 35.13, 37.98, 38.83, 46.12, 48.56, 51.94, 68.10, 69.25, 73.28, 78.17, 83.60, 129.84, 133.58, 137.71, 159.97, 172.04, 177.51, 208.67; IR (neat) $cm^{-1}$: 3422, 1707; MS m/z 531 ($M^+$-H); HRMS Calcd for $C_{31}H_{47}O_7$ Calculated: 531.3322. ($M^+$), measured: 531.3325; $[\alpha]_D^{25}$=+106.69 (c=0.75, $CHCl_3$).

9) Ethylation

Under Ar flow, to anhydrous dichloromethane solution of alcohol form (compound 2 in FIG. 3; 275 mg, 0.43 mmol), 2,6-di-t-butyllutidine (356 mg, 1.74 mmol) and MeOTf (0.134 ml, 1.04 mmol) were added, and stirred at room temperature for 65 hours. Then, the solution was stopped with water, and the organic phase washed with saturated sodium hydrogen carbonate water and saturated sodium chloride was dried over magnesium sulfate and filtered, and then the solvent was distilled off. The residue was separated through silica gel chromatography ($CH_2Cl_2$—AcOEt=4:1) to obtain ethylated form (compound 5b in FIG. 3; 28 mg, 0.0423 mmol, 10%) as colorless oily substance.

$^1$H-NMR ($CDCl_3$): 0.05 (6H,s), 0.89 (9H, s), 1.01 (4H, m), 1.11-1.16 (2H, m), 1.13 (3H, s), 1.22 (3H, s), 1.23-1.27 (14H, m), 1.32 (3H, s), 1.61-1.72 (2H, m), 1.78 (3H, s), 2.28-2.65 (4H, m), 3.17 (1H, br), 3.30-3.40 (1H, m), 3.91-3.99 (3H, m), 5.61-1H, s), 7.47 (1H, s); $^{13}$C-NMR ($CDCl_3$): −4.91, 10.46, 14.42, 15.96, 16.11. 17.47, 18.71, 22.95, 23.61, 25.30, 26.19, 27.48, 29.39, 29.54, 29.68, 30.43, 32.12, 34.42, 35.31, 38.52, 39.00, 46.49, 49.68, 59.35, 68.24, 69.69, 73.74, 78.59, 83.66, 128.85, 133.60, 137.53, 160.56, 177.72; IR (neat) $cm^{-1}$:

3419, 1711; MS m/z 659 (M$^+$-H); HRMS Calcd for C$_{38}$H$_{63}$O$_7$Si Calculated: 659.4343. (M$^+$-H), Measured: 659.4383; [α]$_D^{25}$=+81.97 (c=0.1.20, CHCl$_3$).

10) Desilylation of Ethylated Form

Under Ar flow, anhydrous THF solution of silylated form (compound 5b in FIG. 3; 28 mg, 0.0424 mmol) was cooled with ice, tetra-n-butylammonium fluoride (1 M THF solution, 0.13 ml, 0.13 mmol) was added, and stirred at room temperature for 40 minutes. The reaction was stopped with saturated ammonium chloride aqueous solution, and the organic phase obtained by extracting with chloroform was dried over magnesium sulfate, filtrated and the solvent was distilled out. The residue was separated through silica gel chromatography (AcOEt) to obtain alcohol form (compound 6b (sample NPB-14) in FIG. 3; 17 mg, 0.0317 mmol, 75%) as colorless oily substance.

$^1$H-NMR (CDCl$_3$): 1.01-1.04 (4H, m), 1.14 (3H, s), 1.23-1.32 (14H, m), 1.61-1.68 (2H, m), 1.78 (3H, s), 1.98-2.04 (2H, m), 2.32-2.39 (2H, m), 2.97 (1H, br), 3.17 (1H, br), 3.28-3.35 (1H, m), 3.43-3.49 (1H, m), 3.99-4.01 (3H, m), 5.63 (1H, s), 7.48 (1H, s); $^{13}$C-NMR (CDCl$_3$): 10.49, 14.42, 15.91, 16.11, 17.61, 22.95, 23.61, 25.30, 25.90, 27.51, 29.39, 29.54, 29.67, 32.12, 34.42, 35.18, 38.63, 39.08, 46.51, 49.67, 59.39, 68.43, 69.63, 73.72, 78.67, 83.70, 130.14, 133.89, 138.05, 160.57, 177.74, 209.16; IR (neat) cm$^{-1}$: 3449, 1708; MS m/z 546 (M$^+$); HRMS Calcd for C$_{32}$H$_{50}$O$_7$ Calculated: 546.3557. (M$^+$), Measured: 546.3548; [α]$_D^{25}$=+109.81 (c=0.745, CHCl$_3$).

Example 2

Anti-HIV Effect

<Cell Culture>

For this experiment, human T-cell leukemia virus I (HTLV-I) infected T cell strain, MT-4 cell and T cell leukemia cell strain, MOLT-4 (clone No. 8) cell, HIV-1 continuous infection cell, MOLT-4/IIIB cell were used. The cell was cultured in RPMI-1640 medium (SIGMA) supplemented with 10% inactivated fetal calf plasma (FCS) (MOREGATE, Australia), 100 μg/ml streptomycin and 100 U/ml penicillin G (SIGMA) under a condition of 5% CO$_2$ and 37° C. Subculture was performed every three days by controlling the density to 30×10$^4$ cells/ml.

<Virus>

As virus, HIV-1 IIIB strain (T cell tropic strain: T-tropic) and HIV-1JRCSF (macrophage tropic: M-tropic) were used. HIV-1 IIIB was prepared from the supernatant of MOLT-4/IIIB cell.

MOLT-4/IIIB cell was controlled to a density of 30×10$^4$ cells/ml and then the culture was started. The cultured liquid was collected three days later, and centrifuged at 3000 rpm for 10 minutes at 4° C. JRCSF was obtained by culturing 293T cell transfected with 15 μg of virus DNA and collecting the cultured liquid two days later. These supernatants were passed through 0.45 μm filter. The virus stocks were frozen and stored at −80° C. The amount of virus was adjusted depending on an amount of p24.

<Sample to be Tested>

1) in vitro activity: A phorbol derivative was dissolved in an amount of 1.0 mg in 1.0 ml of DMSO to obtain a concentrated solution. A sample to be tested was prepared by diluting the concentrated solution with a saline or a phosphate buffer to a predetermined concentration.

2) stability in blood: 1 ml of blood from the abdominal aorta of 6- to 7-week-old BALB/c male mouse was withdrawn in an injector in which 0.1 ml of 3.8% sodium citrate was contained, and centrifuged at 5000 rpm for 10 minutes to obtain a plasma. The plasma was added in a solution to be tested in a proportion of 9:1 to prepare a diluted solution to be tested in a predetermined concentration of 10-fold dilution. The diluted solution was incubated at 37° C. for 30 minutes to prepare a sample to be tested.

3) in situ activity: the above-mentioned sample to be tested 1) was orally administered to 6- to 7-week-old BALB/c male mouse in a dose of 1 mg/kg, at 20, 40 and 60 minutes after the administration, blood was withdrawn from the abdominal aorta under light anesthetization similarly to those of the 2) above, and the plasma from the blood was used as a sample to be tested. For assay, the sample was inactivated at 56° C. for 30 minutes, and then added in a concentration of 1-10%.

<Evaluation of Anti-HIV Activity>

The anti-HIV activity of each sample to be tested was evaluated by measuring inhibition activity against cytopathogenicity induced by HIV-1 according to MTT assay. The assay was performed in a triplicate mode, and anti-HIV activity and cytotoxicity were measured simultaneously.

96-well plate was used, 10% FCS/RPMI-1640 medium was added in inner 60 wells in an amount of 100 μl/well, and in outer 36 wells in an amount of 200 μl/well in order to prevent evaporation.

The samples to be tested that were adjusted with RPMI-1640 medium were added in an amount of 25 μl/well in the first lane of the inner 60 wells, and 5-fold stepwise dilution series were prepared by manipulating pipette. In addition, in the last lane, no sample to be tested was added and regarded as control. MT-4 cell suspended in 30×10$^4$ cells/ml was prepared in two flasks, and the cells in one flask were infected with HIV-1 IIIB in a multiplicity of infection (MOI) of 0.01. The infected or non-infected MT-4 cells were immediately added to samples to be tested in an amount of 100 μl/ml, and cultured under a condition of 5% CO$_2$ and 37° C.

5 days later, the viability of cells was measured based on MTT method by use of Titertek Multiskan. MTT adjusted to 7.5 mg/ml with PBS (Ca++, Mg++*free phosphate-buffered saline) was added in an amount of 20 μl/well, and cultured under a condition of 5% CO$_2$ and 37° C., 150 μl of the cultured supernatant was removed and then 100 μl of cytolysis solution (5% (v/v)TritonX-100/acid isopropanol) was added and stirred on a plate mixer for 30 minutes.

The absorbance (reference wavelength: 690 nm) was determined with a plate reader at 540 nm. The viability (% of control) of each well was calculated by regarding the average of absorbance in case where neither sample to be tested nor virus as 100%, and the average of absorbance in case where no sample to be tested was added and virus was added as 0%, and 50% cytotoxic concentration: CC$_{50}$ and 50% effective concentration: EC$_{50}$ were determined. Further, ratio of CC$_{50}$ to EC$_{50}$, that is, selective index (SI=CC$_{50}$/EC$_{50}$) was calculated.

The infection to peripheral blood mononuclear cells (PBMC) of JRCSF and the evaluation of the anti-HIV activity were performed as follows. 1×10$^6$ cells/ml of PBMC was inoculated with JRCSF having 20 ng of p24, and the cells were washed 2 hours later. Thereafter, the cells were cultured in a culture liquid containing an agent to be tested for 7 days, and the antiviral activity was detected by measuring p24.

<Results>

The anti-HIV activity of a series of phorbol derivatives in vitro is shown in Table. N-6 that is a diester of phorbol and has an acetyl group at 12-position and a decanoyl group at 13-position (S. El-Mekkawy et al.; Chem. Pharm. Bull. 47(9) 1346-

1347 (1999)) showed an extremely strong anti-HIV activity but lost the activity in plasma and was unstable in living organism. It is presumed that the ester at 12-position may be hydrolyzed by pseudo choline esterase in blood.

Thus, the substituents at 12-position were considered in order to produce stable derivatives in living organism. NPB-5 and NPB-9 in which the substituent at 12-position has been changed into ester type increased in the number of carbon, contrary to what we expected, was lowered in the activity.

On the other hand, NPB-11 in which the substituent at 12-position was changed into methoxymethyl group being ether type had a strong activity and was stable in blood. However, NPB-12 in which the substituent at 12-position was changed into methoxyethyl group increased in the number of carbon by one was lowered in the activity.

In addition, NPB-13 and NPB-14 in which the substituent at 12-position was changed into methoxy group and ethoxy group, respectively had a weak activity and was unstable to heat compared with NPB-11.

The synthesis of derivatives in which several substituents were introduced to 12-position of basic compound N-6 allowed to produce NPB-11 that is stable to heat and also biologically stable, and that 50% inhibition concentration of anti-HIV activity thereof is as extremely low as 1.7 ng/ml, on the contrary to normal cells, 50% injury concentration is as high as 6.9123 µg/ml, therefore safety index is 4066.

processes (3) and (5), and the therapy is centered on a cocktail therapy by use of three agents in which two agents for blocking the process (3) and one agent for blocking the process (5) are simultaneously used. However, it is difficult to completely cure AIDS because the virus repeats mutation successively. In the meanwhile, although the agent for blocking the process (1) is being developed, it has not been used as a therapeutic agent yet.

As the products of the present invention are effective for virus strains that direct toward two different co-receptors in the process (1), it is thought that the present products can be used not only alone but also in a combination with any agent acting to other process, and therefore have a high usability.

INDUSTRIAL APPLICABILITY

The antiviral preparations of the present invention may be composed of a specific phorbol derivative and an agent having another anti-HIV effect that is different in the mechanism of action with that of the phorbol derivative. Therefore, the present preparations can exert plural antiviral effects through different mechanisms of action to provide a very strong antiviral effect. In addition, as the antiviral preparations of the present invention can contain any antidotes or any antiviral agents other than the phorbol derivative of formula 1, the preparations have no harmful side effects and are effective for

TABLE

Antiviral effect of phorbol derivative in MT-4 cell infected with T-cell tropic strain (HIV-1 IIIB)

| Sample No. | Structural formula Side chain at 12-position | Anti-HIV Activity $EC_{50}$ ng/ml | Cytotoxicity $CC_{50}$ µg/ml | Safety Index S.I. $CC_{50}/EC_{50}$ | Heat Stability 56° C., 30' | Biological Stability |
|---|---|---|---|---|---|---|
| N-6 | —OCOCH$_3$ | 1.7 | 3.2638 | 1920 | Stable | Unstable |
| NPB-5 | —OCOCH$_2$CH$_3$ | >1000 ng | 125 | 125< | — | — |
| NPB-9 | —OCOCH$_2$CH$_2$CH$_3$ | >1000 ng | 125 | 125< | — | — |
| NPB-11 | —OCH$_2$OCH$_3$ | 1.7 | 6.9123 | 4066 | Stable | Stable |
| NPB-12 | —OCH$_2$CH$_2$OCH$_3$ | 3.72 | 3.2817 | 882 | Stable | Stable |
| NPB-13 | —OCH$_3$ | 118.9 | 4.6173 | 39 | Unstable | Stable |
| NPB-14 | —OCH$_2$CH$_3$ | 195.7 | 3.3240 | 17 | — | Stable |

The anti-HIV activity shown in Table was evaluated by use of the virus of T-cell tropic strain, and the evaluation is an assay system through which a second receptor CXCR4 is mediated in the process of adsorption and invasion of virus to host cell. Currently, there are two types in which cells are infected with HIV virus, in another type other than the above-mentioned one, it is supposed that CCR5 is mediated as the second receptor contained in macrophage tropic virus.

Then, in order to make clear whether or not a phorbol derivative is associated with CCR5 receptor, NPB-11 was examined.

Figure 4:
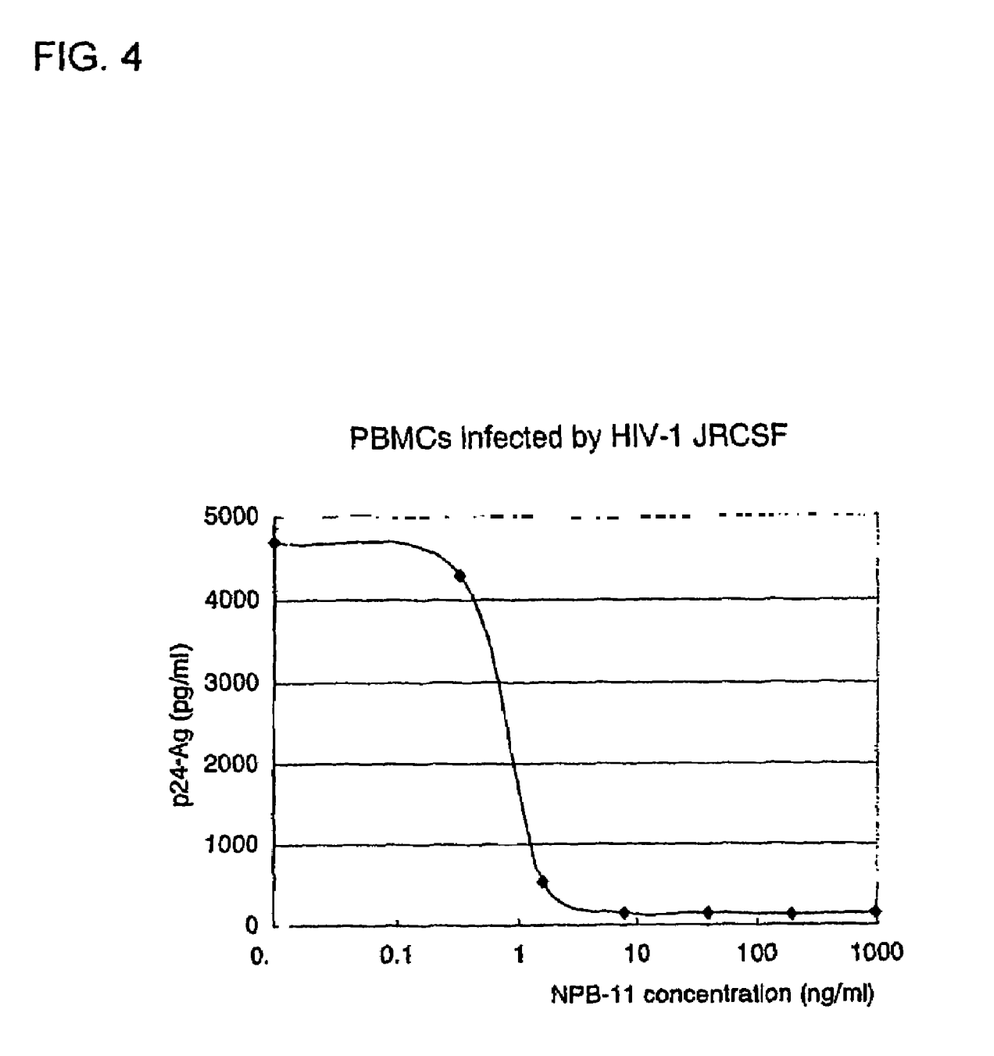
FIG. 4 is a graph showing the antiviral effect of NPB-11.

FIG. 4 shows the antiviral effect of NPB-11 in peripheral lymphocytes infected with macrophage tropic strain (HIV-1 JRCSF). The anti-HIV effect was evaluated by determining the amount of p24 that is one of viral gap proteins and calculating its reduced amount. In case where NPB-11 was used in a concentration of 1 ng/ml, little viral protein was detected, and therefore clear antiviral effect was recognized.

AIDS virus is replicated and propagated by repeating the life cycle of (1) adsorption to host cells, (2) invasion/uncoating, (3) reverse transcription of viral gene and integration, (4) transcription/replication of viral gene, (5) protein synthesis and modification, (6) particle formation and release.

If one process in the cycle is blocked, it is able to inhibit the propagation of virus. Currently, there are agents that block the many viruses. Therefore, the antiviral preparations of the present invention are useful for particularly anti-HIV drugs.

The invention claimed is:

1. A composition comprising as an active ingredient, at least a phorbol derivative of formula 1:

wherein
R$_1$ is
a group of —(CH$_2$)$_a$X(CH$_2$)$_b$CH$_3$ wherein X is O or S, a is a number of 1 to 3, and b is a number of 0 to 5, or a group of —$(CH_2)_cX(CH_2)_dYCH_3$ wherein X and Y are O or S, c is a number of 1 to 3, and d is a number of 1 to 5, $R_2$ is a group of —$CO(CH_2)_nCH_3$ wherein n is a number of 3 to 12, and $R_3$, $R_4$ and $R_5$ are independently of one another, hydrogen atom, or an acetyl, benzyl, or tigloyl carboxylic acid residue, and having a specific safety index S.I.=$CC_{50}/EC_{50}$ of 10 or more wherein $EC_{50}$ means a concentration at which HIV-1 induced cytopathogenic effect (CPE) in MT-4 cell is inhibited by 50%, and $CC_{50}$ means a concentration at which survival of MT-4 cell in a cell proliferation test is reduced by 50% and a pharmaceutically acceptable excipient.

2. The composition of claim 1, wherein $R_1$ in formula 1 is a group of —$(CH_2)_aX(CH_2)_bCH_3$ wherein X is O or S, a is a number of 1 to 3, and b is a number of 0 to 5.

3. The composition of claim 1, wherein $R_1$ in formula 1 is a group of —$(CH_2)_cX(CH_2)_dYCH_3$ wherein X and Y are O or S, c is a number of 1 to 3, and d is a number of 1 to 5.

4. An anti-HIV virus preparation comprising at least one of phorbol derivatives of formula 1 according to claim 1, and at least one of other agents having anti-HIV effect.

5. The anti-HIV virus preparation according to claim 4, characterized in that the other agent having anti-HIV effect is a reverse transcriptase inhibitor.

6. The anti-HIV virus preparation according to claim 4, characterized in that the other agent having anti-HIV effect is an agent that inhibits an integration of DNA mediated by an integrase.

7. The anti-HIV virus preparation according to claim 4, characterized in that the other agent having anti-HIV effect is an agent that suppresses a transcription of provirus.

8. The anti-HIV virus preparation according to claim 4, characterized in that the other agent having anti-HIV effect is an agent that inhibits a synthesis of core protein mediated by a protease.

9. The anti-HIV virus preparation according to claim 4, characterized in that the other agent having anti-HIV effect is an agent that suppresses an assembly and packaging of core proteins.

10. The anti-HIV virus preparation according to claim 4, characterized in that the other agent having anti-HIV effect is an agent that suppresses an aggregation of core proteins and extra-shell proteins.

11. The anti-HIV virus preparation according to claim 4, characterized in that the other agent having anti-HIV effect is an agent that suppresses a maturity of infectious virus particles released and escaped from cell membrane.

* * * * *

UNITED STATES PATENT AND TRADEMARK OFFICE
CERTIFICATE OF CORRECTION

PATENT NO. : 7,662,852 B2 Page 1 of 1
APPLICATION NO. : 10/557922
DATED : February 16, 2010
INVENTOR(S) : Masao Mori et al.

It is certified that error appears in the above-identified patent and that said Letters Patent is hereby corrected as shown below:

Title page,

Replace Item (75), to read as follows:

--(75) Inventors: Masao Mori, Toyama (JP); Haruo Saito, Toyama (JP); Hideo Nemoto, Toyama (JP); Naoki Yamamoto, Ota-ku, Tokyo (JP); Masao Hattori, Toyama (JP)--

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,662,852 B2
APPLICATION NO. : 10/557922
DATED : February 16, 2010
INVENTOR(S) : Mori et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 988 days.

Signed and Sealed this

Thirtieth Day of November, 2010

David J. Kappos
*Director of the United States Patent and Trademark Office*